United States Patent
Dunn et al.

(10) Patent No.: US 10,441,826 B2
(45) Date of Patent: Oct. 15, 2019

(54) AIRFLOW CONTROL VALVE

(71) Applicant: Joseph Anthony Griffiths, Hampshire (GB)

(72) Inventors: Philip Dunn, Hampshire (GB); Tamas Palinkas, Hampshire (GB)

(73) Assignee: Joseph Anthony Griffiths, Hampshire (GB)

( * ) Notice: Subject to any disclaimer, the term of this patent is extended or adjusted under 35 U.S.C. 154(b) by 1340 days.

(21) Appl. No.: 14/382,150

(22) PCT Filed: Feb. 13, 2013

(86) PCT No.: PCT/EP2013/052823
§ 371 (c)(1),
(2) Date: Aug. 29, 2014

(87) PCT Pub. No.: WO2013/127627
PCT Pub. Date: Sep. 6, 2013

(65) Prior Publication Data
US 2015/0083133 A1    Mar. 26, 2015

(30) Foreign Application Priority Data
Feb. 29, 2012    (GB) .................................. 1203491.4

(51) Int. Cl.
*A62B 7/04*    (2006.01)
*A62B 9/02*    (2006.01)
(Continued)

(52) U.S. Cl.
CPC .............. *A62B 7/04* (2013.01); *A61M 39/223* (2013.01); *A62B 9/02* (2013.01); *A62B 18/02* (2013.01);
(Continued)

(58) Field of Classification Search
CPC .......... A61M 2039/224; A61M 39/223; A61M 16/0069; A61M 16/00; A61M 16/0003;
(Continued)

(56) References Cited

U.S. PATENT DOCUMENTS 3,599,636 A  *  8/1971  Gutman .............. A62B 18/084
                                                        128/207.11
3,654,958 A  *  4/1972  Bitonti ................ F15B 13/0402
                                                        137/596.14
(Continued)

FOREIGN PATENT DOCUMENTS

GB        2430159           3/2007
GB        2430159 A  *      3/2007    ............ A61M 16/06

OTHER PUBLICATIONS

"International Search Report for PCT/EP2013/052823 dated May 23, 2013".

*Primary Examiner* — Tan-Uyen T Ho
*Assistant Examiner* — Victoria Murphy
(74) *Attorney, Agent, or Firm* — Kramer Amado, P.C.

(57) ABSTRACT

An airflow control valve (20) for use in a breathing apparatus (10) to control a flow of air from a pressurized air supply to a respirator. The valve comprises an inlet port (31) for connection to a pressurized air supply, and first (32) and second (33) outlets. The valve is configurable between a first position in which the inlet port is in restricted fluid communication with the first outlet to allow a restricted flow of air from the inlet port to the first outlet and in which the second outlet is sealed from the inlet port and, a second position in which the inlet port is in substantially unrestricted fluid communication with the second outlet to allow an unrestricted flow of air from the inlet port to the second outlet.

29 Claims, 4 Drawing Sheets

(51) Int. Cl.
*A62B 18/08* (2006.01)
*A62B 18/10* (2006.01)
*F16K 11/07* (2006.01)
*F16K 17/04* (2006.01)
*A61M 39/22* (2006.01)
*A62B 18/02* (2006.01)

(52) U.S. Cl.
CPC ............ *A62B 18/084* (2013.01); *A62B 18/10* (2013.01); *F16K 11/0716* (2013.01); *F16K 17/0473* (2013.01); *A61M 2039/224* (2013.01); *Y10T 137/86485* (2015.04); *Y10T 137/86702* (2015.04)

(58) Field of Classification Search
CPC .... A61M 16/06; A61M 16/20; A61M 16/107; A61M 16/1055; A61M 2205/3327; A61M 2205/52; A61M 2016/003; A61M 2230/40; A61M 2016/0027; A61M 2205/3334; A61M 2205/505; A61M 2205/3317; A61M 2016/0021; A61M 16/0683; A61M 16/204; A61M 2205/587; A61B 5/097; A61B 5/087; A61B 5/0803; A61B 5/4842; A62B 18/10; A62B 9/02; A62B 9/022; A62B 9/025; A62B 9/027; Y10T 137/86694; Y10T 137/86702; F16K 11/0716; A63B 21/0004; A63B 23/18
See application file for complete search history.

(56) References Cited

U.S. PATENT DOCUMENTS

| | | | | |
|---|---|---|---|---|
| 4,437,462 A | * | 3/1984 | Piljay | A62B 18/084 128/207.11 |
| 4,915,106 A | * | 4/1990 | Aulgur | A62B 18/084 128/205.24 |
| 5,036,846 A | * | 8/1991 | Aulgur | A62B 18/084 128/205.24 |
| 5,183,037 A | * | 2/1993 | Dearman | A61M 16/20 128/204.18 |
| 5,375,625 A | | 12/1994 | Reynolds | |
| 5,623,923 A | * | 4/1997 | Bertheau | A62B 18/084 128/201.22 |
| 5,690,102 A | * | 11/1997 | Bertheau | A62B 18/084 128/205.24 |
| 5,944,054 A | | 8/1999 | Saieva | |
| 6,039,045 A | * | 3/2000 | Bertheau | A62B 18/084 128/206.27 |
| 2018/0361179 A1 | * | 12/2018 | Sibuet | A62B 27/00 |

* cited by examiner

AIRFLOW CONTROL VALVE

The present invention relates to a control valve for use with a breathing apparatus.

Various types of breathing apparatuses are known in the art, including those for use in situations where there has been a sudden hazardous leak of gas or toxic airborne particles that would injure a person if inhaled. Such breathing apparatuses are known as 'escape sets', and generally comprise a bag or other container containing a mask and/or hood (generally called a 'respirator' hereafter) connected via a hose and a valve means to a source of breathable air in a high-pressure compressed air cylinder. In an emergency situation, a user dons the respirator, which, in the case of a mask, makes a seal with his face or, in the case of a hood, seals around his neck enclosing his head, and allows him to breathe from the air supply, isolated from the harmful atmosphere. The valve means is provided between the cylinder and the respirator to reduce the high pressure from the cylinder to a pressure suitable for the wearer to breathe. These escape sets are provided in environments where there is a possibility of such a hazardous leak occurring, such as chemical plants or oil platforms, in convenient locations so that if a hazardous leak occurs, the people in the vicinity of the leak can quickly get to an escape set and don the respirator to allow them to leave the hazardous area and get to safety. Other types of known breathing apparatuses include those known as 'working sets' and 'self contained breathing apparatuses', which include respirator and compressed air supply generally as described above, which a user can don to enable him to safely breathe clean uncontaminated air from the compressed air supply in environments in which the ambient atmosphere is unsafe to breathe.

The valve means provided in such breathing apparatuses generally comprises a 'reducer' which reduces the pressure in the hose from the high pressure in the cylinder (typically around 200-300 bar) to a much lower pressure, (around 8 bar), and a 'demand valve' which supplies air from the reducer and the hose, to the respirator at a pressure suitable to breathe.

When the breathing apparatuses are not in use, they may be stored in a container in a state of readiness. In the case of escape sets, the situations in which they are required are often ones of extreme danger and the time it takes a user to don the respirator and activate the air-flow is critical. It is therefore imperative that the escape set is designed so that the respirator can be donned as quickly as possible. To help initiate the air supply quickly, some escape sets have an automatic activation system in which, prior to use, the reducer is closed and seals the compressed air supply from the respirator, but when the respirator is removed from the container the reducer is opened and the supply of air to the respirator is activated. This can be effected by, for example, a cord secured at one end to the container and at the other end to an activation switch on the respirator. In the case of other types of breathing apparatuses, it is also generally desirable that the respirator can be donned and the air supply activated as quickly as possible for convenient and efficient use.

When a wearer first dons a respirator in a toxic atmosphere, some of the toxic atmosphere will be trapped inside the respirator cavity, meaning that his first breath will involve inhaling some of the toxic gas. It is therefore desirable to have a constant but steady and controlled flushing flow of air out of the respirator prior to a user taking his first breath therefrom, so when the respirator is first donned, the flushing flow purges the respirator cavity of any toxic atmosphere that may have been trapped therein but does not waste the supply of air.

Conventional breathing apparatuses, such as those described above, comprise an arrangement of harness straps and buckles which need to be loosened to allow the wearer to fit the respirator over his head, and then once in place, tightened to secure the respirator in place tight enough against the face, in the case of a respirator mask, and/or around the neck in the case of a respirator hood, to maintain a seal therewith. As mentioned above, in the case of escape sets, these are intended for use in emergency situations which are hazardous and stressful. It is therefore important that the respirator is able to be donned and secured in place as quickly and easily as possible, and that the attachment arrangement is as simple as possible to operate in order to prevent panicked fumbling in trying to don the respirator. Conventional strap and buckle harnesses are problematic in that their fitment is relatively slow and complicated, and so increases the time during which the wearer is at risk from the harmful atmosphere. In the case of all such breathing apparatuses, it may be difficult to tell whether the respirator has been correctly fitted, and so it may leak and waste valuable air from the cylinder, reducing the available breathing time from a given compressed air supply volume, which in the case of use in emergency or hazardous environments, limits the escape time or the time the wearer can remain in that environment before having to get to safety.

In an attempt to solve the problems mentioned above, breathing apparatuses have been proposed that comprise a respirator, an inflatable harness for securing the respirator to a wearer's head and a method of controlling the flow of air from a supply to the respirator and to the inflatable harness, wherein the breathing apparatus is configured so that the head harness automatically inflates and expands prior to the respirator being secured to the wearer's head, and automatically deflates and contracts once the respirator is sealed on the wearer's head. Such a breathing apparatus is disclosed in UK patent application No. 0611646.1 which includes a control valve to control the flow of air from a supply to the respirator and to the inflatable harness The present invention seeks to provide an alternative and/or improved control valve for use in an emergency breathing apparatus and a breathing apparatus including such a control valve.

According to the invention, there is provided an airflow control valve for use in a breathing apparatus to control a flow of air from a pressurised air supply to a respirator, wherein the valve comprises an inlet port for connection to a pressurised air supply, and first and second outlets, the valve being configurable between a first position in which the inlet port is in restricted fluid communication with the first outlet to allow a restricted flow of air from the inlet port to the first outlet and in which the second outlet is sealed from the inlet port and, a second position in which the inlet port is in substantially unrestricted fluid communication with the second outlet to allow an unrestricted flow of air from the inlet port to the second outlet. That is, the airflow control valve is configured to allow a flow of air from the inlet port to the first outlet at a first, reduced, flow rate, when the valve is in the first position, and allow a flow of air from the inlet port to the second outlet at a second flow rate greater than the first flow rate, when the valve is in the second position.

The airflow control valve may be configured such at the first outlet is sealed from the inlet port when the valve is configured in the second position. The airflow control valve may also include a third outlet and be configured such that, in the first position, the inlet port is in fluid communication with the third outlet.

The airflow control valve may be configured such that, in the second position, the inlet port is sealed from the third outlet.

The airflow control valve may be configurable to a third position in which the inlet port is in restricted fluid communication with the first outlet and the inlet port is sealed from the second outlet and/or third outlet, and the third valve position may be intermediate the first and second valve positions.

The airflow control valve may further comprise a fourth outlet which may be in fluid communication with the third outlet when the valve is configured in the second position, and is sealed from the third outlet when the valve is configured in the first and third positions.

The airflow control valve may be movable between the first, second and/or third positions in dependence of the air pressure within the valve.

The airflow control valve may comprise a valve housing defining a piston chamber and, a piston received within the piston chamber, wherein the piston is slidable within the piston chamber between the respective valve positions.

The inlet port and respective outlets may be formed in the valve housing in fluid communication with the piston chamber. The piston may include a hollow bore in fluid communication with the inlet port.

The piston may comprise a piston shaft and a piston head, wherein the hollow bore extends along the longitudinal axis of the piston shaft and a portion of the piston head The piston may include a plurality of channels formed therein in fluid communication with the hollow bore and extending to an outer surface of the piston, and which are configured to selectively fluidly communicate the inlet port and the hollow bore with the outlets in the valve housing.

The piston may comprise a first channel configured to fluidly communicate the inlet port with the third outlet via the hollow bore when the piston is in the first position. The piston may also comprise a second channel configured to fluidly communicate the inlet port with the first outlet via the hollow bore when the valve is in the first position, and to fluidly communicate the inlet port with the second outlet via the hollow bore when the piston is in the second position.

The second channel may be in restricted fluid communication with the first outlet via the hollow bore when the piston is in the intermediate position.

The piston may comprise a plug member configured to block the fourth outlet when the piston is in the first and third positions and to open the fourth outlet to allow flow of air therethrough when the piston is in the second position.

The valve housing may comprise a passage of restricted cross-sectional area which is in fluid communication with the fast outlet and the piston chamber, and which is configured to allow a restricted flow of compressed air from the inlet port to the first outlet when the valve is in the first position.

Said passage may comprise a second passage and the valve housing may further comprise first and third passages configured to fluidly communicate the inlet port with the third and second outlets respectively when the piston is in the first and second positions respectively.

The airflow control valve may further comprise a biasing means configured to bias the piston towards the first position.

The piston may comprise a plurality of piston surfaces configured such that pressurised air supplied to the inlet port can act upon one or more of the piston surfaces to exert a force against the force of the biasing means. The valve may be configured so that the piston slides from the first position to the third position when the an pressure acting on a first piston surface teaches a first pre-determined value.

The airflow control valve may be configured so that the piston slides, from the third position, into the second position when the air pressure acting on the second piston surface reaches a second pre-determined value.

The airflow control valve may further comprise a sensing valve fluidly connected to the first outlet and configured to close when an air pressure at the first outlet teaches a pre-determined threshold pressure.

The present invention also provides a breathing apparatus comprising a respirator and a control valve to control the flow of air from a supply to the respirator, wherein the control valve comprises an inlet port for connection to a pressurised air supply, and first and second outlets connected to the respirator, the valve being configurable between a first position in which the inlet port is in restricted fluid communication with the first outlet to allow a restricted flow of air from the inlet port to the respirator via the first outlet and in which the second outlet is sealed from the inlet port and, a second position in which the inlet port is in substantially unrestricted fluid communication with the second outlet to allow an unrestricted flow of air from the inlet port to the respirator via the second outlet.

The control valve may be configured such that when in the second position, the first outlet is sealed from the inlet port.

The breathing apparatus may further comprise an inflatable harness for securing the respirator to a wearer's head, the control valve further being configured to control the flow of air from a supply to the inflatable harness.

The airflow control valve may further comprise a third outlet connected to the inflatable harness, wherein the inlet port is in fluid communication with the harness when the control valve is in the first position and wherein the inlet port is sealed from the inflatable harness when the control valve is in the second position.

The airflow control valve may be configurable to a third position in which the inlet port is in restricted fluid communication with the respirator via the first outlet and the inlet port is sealed from the second outlet and/or third outlet.

The airflow control valve may comprise any of the features described above.

The fourth outlet may be open to the atmosphere.

The first pre-determined pressure may be reached when the inflatable harness is fully inflated.

The piston head may comprise a first, second and third portions integrally formed and sequentially radially enlarged around the axis of the piston head, and the piston shaft extends from the third portion.

The first, second and third portions may comprise first, second, and third surfaces disposed perpendicular to the longitudinal axis of the hollow bore, wherein the volumes of space enclosed between the valve housing and the first, second and third surfaces comprise first, second and third chambers respectively.

Preferred embodiments of the present invention will now be described, by way of example only, with reference to the accompanying drawings, in which.

Figure 1:
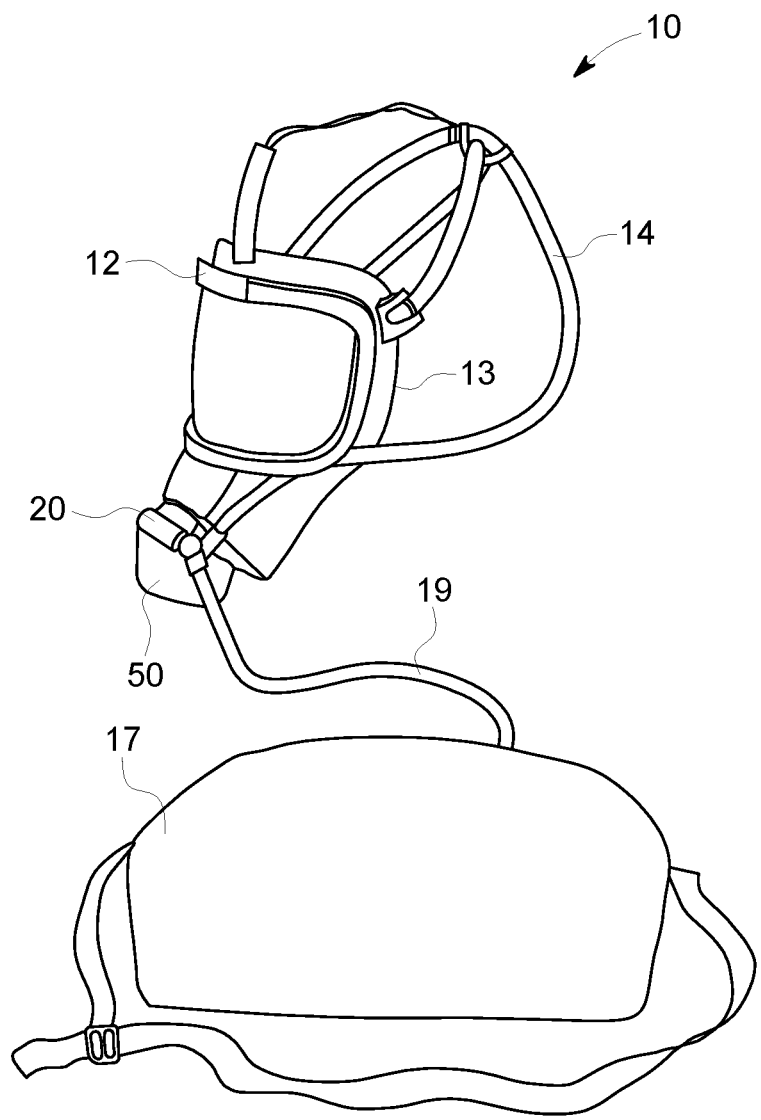
FIG. 1 is a perspective view of a breathing apparatus of relevant to the present invention.

Referring now to FIG. 1, an emergency breathing apparatus 10 including an air control valve 20 of the present invention is shown. The breathing apparatus 10 comprises a respirator mask 12 and an inflatable harness 14 to secure the respirator 12 to a wearer's head. The respirator 12 has a seal 13 around its peripheral edge that, in use, makes a substantially air-tight seal around the wearer's face. The respirator 12 and harness 14 are fluidly connected to a source of compressed air (not shown) by a supply hose 19 via the control valve 20 on the front of the respirator 12. The respirator 12 also includes a positive pressure exhalation valve (not shown) to allow air exhaled by a wearer to be expelled from the respirator 12, a sensing valve 80 to detect when the respirator is substantially sealed to the wearer's face and a demand valve 50 to allow air into the respirator 12. The whole breathing apparatus 10, including the compressed air supply, is contained within a bag 17 made of suitably tough material, such as PVC coated weatherproof material, or possibly an anti-static material if the apparatus is to be used in potentially explosive environments.

Figure 2:
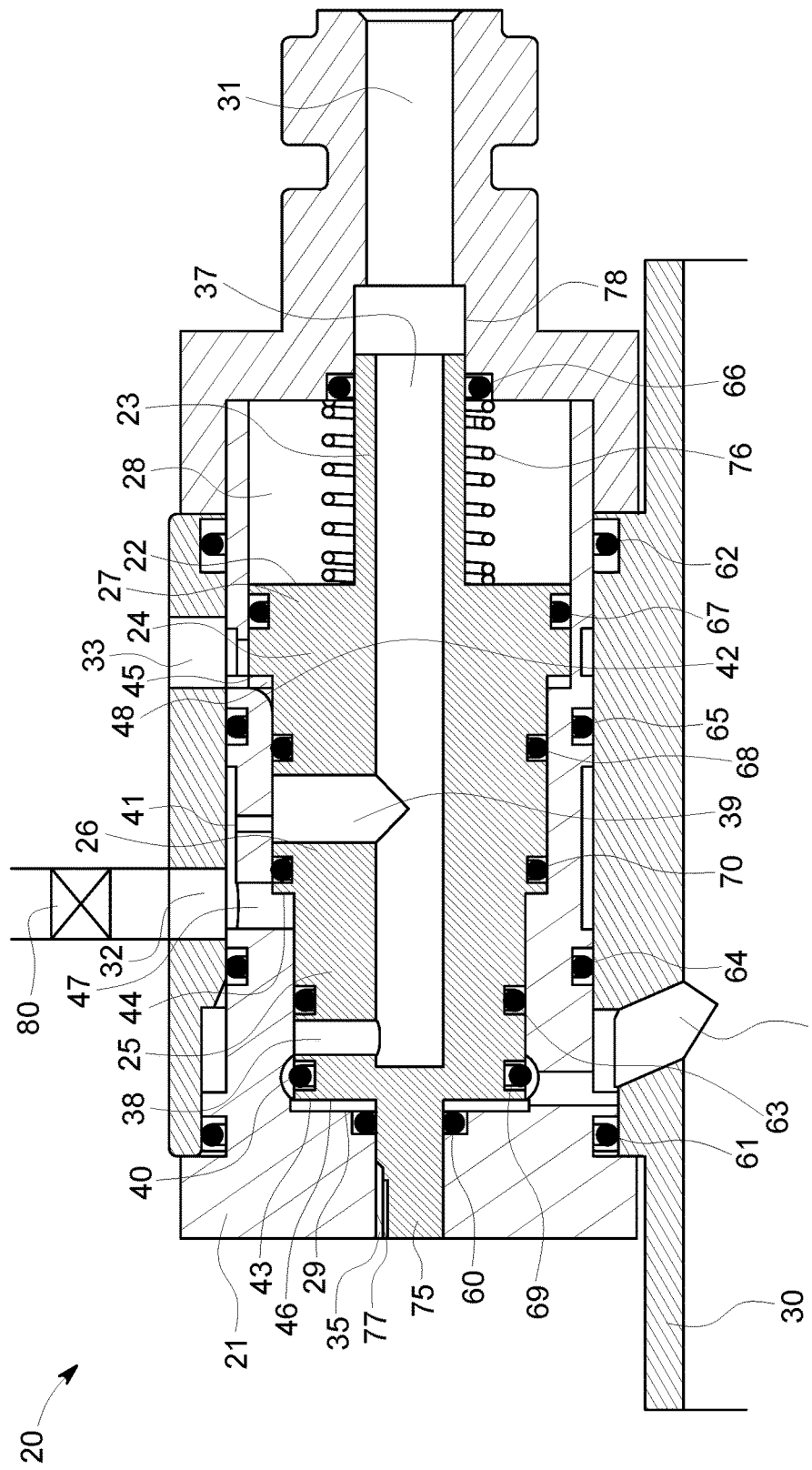
FIG. 2 is a schematic cross-sectional view of a control valve of the present invention of the breathing apparatus of FIG. 1, in a first position.
Figure 3:
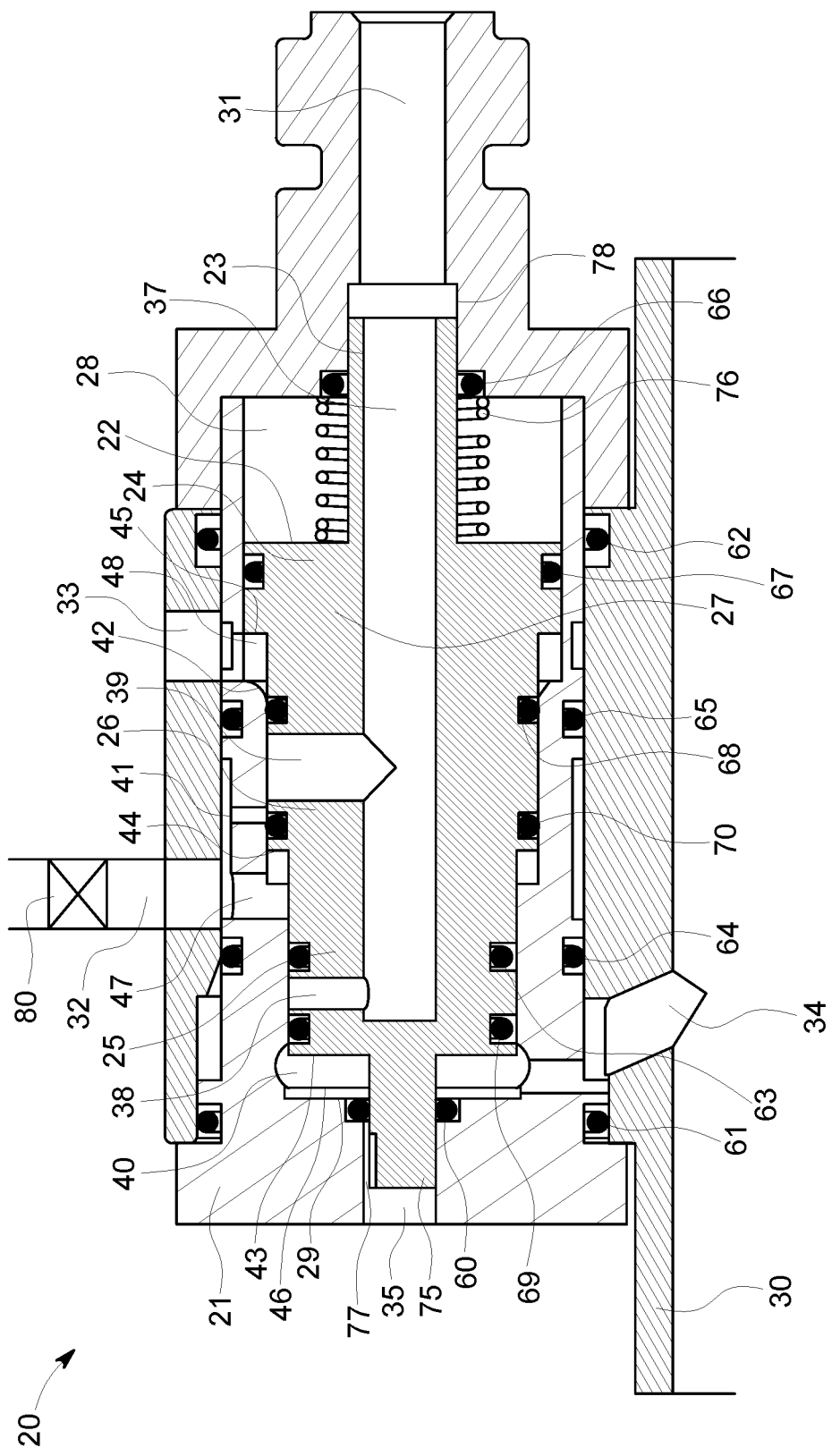
FIG. 3 is a view of the control valve of FIG. 2, in a third or intermediate position.
Figure 4:
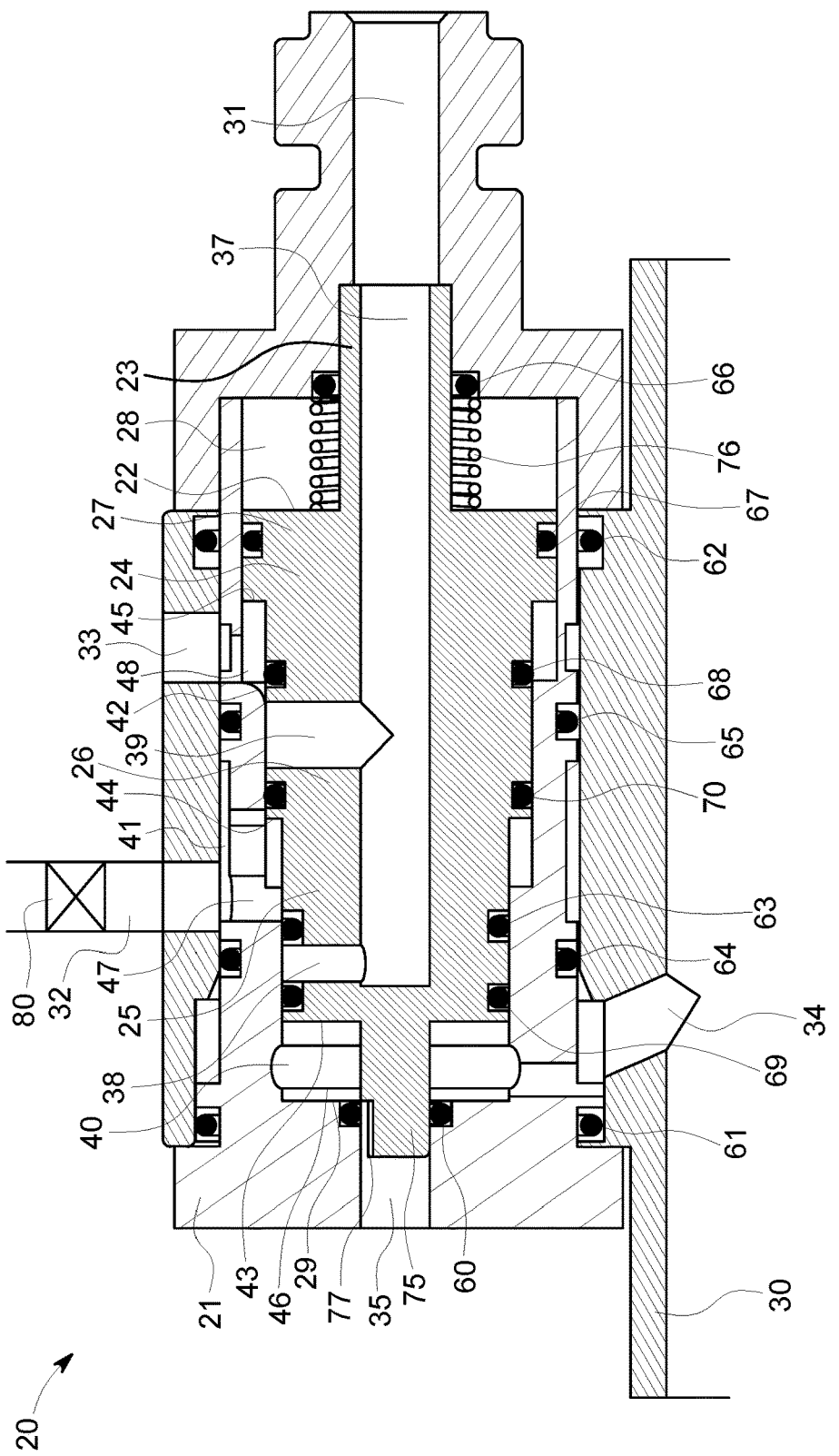
FIG. 4 is a view of the control valve of FIG. 2, in a second position.

The control valve 20 is shown in detail in FIGS. 2-4, and comprises a piston 22, located inside a valve housing 21 which is contained within a valve outer casing 30. The control valve 20 has an inlet port 31 that is fluidly coupled to compressed air supply (not shown). The control valve has a first outlet 32 fluidly coupled to the respirator 12 via a sensing valve 80 for the supply of compressed air via the sensing valve 80 to the inside of the respirator 12. The control valve 20 also has a second outlet 33 fluidly coupled to the demand valve 50 of the respirator. The control valve 20 further comprises a third outlet 34 fluidly coupled to the inflatable harness 14, and a fourth outlet 35, that is open to atmosphere.

The piston comprises a cylindrical piston head 24, comprising a first, second and third piston sections 25, 26, 27, of sequentially increasing diameter, and a piston shaft 23 that is integrally formed with the piston head 24 and extends axially from the third piston section 27 into a correspondingly shaped recess 78 formed in the inlet port 31. The piston also includes a plug shaft 75 which extends axially from the first piston section 25 and which is received in the fourth outlet 35. The valve housing 21 encloses a central piston chamber 28, wherein the portion of the piston chamber 28 distal to the inlet port 31 is the same shape as the piston head 24, but with slightly larger dimensions so that the piston head 24 fits snugly into the piston chamber 28 and is encompassed by the valve housing 21.

The end surfaces of the first, second and third piston sections 25, 26, 27, that are each distal to the piston shaft 23, comprise a first, second and third piston surfaces 43, 44, 45 respectively. The volumes of space encompassed by the valve housing 21 and the first, second and third piston surfaces 43, 44, 45 comprise first, second and third chambers 46, 47, 48 respectively.

The piston 22 is slidable within the valve housing 21 between a first and a second position (shown in FIGS. 2 and 4 respectively), and a third position intermediate the first and second positions (shown in FIG. 3 and hereinafter referred to as the 'intermediate position'), to selectively allow compressed air to flow from the inlet port 31 to the first, second and third chambers 46, 47, 48, and thereby to the third, first and second outlet ports 34, 32, 33, respectively.

The piston 22 includes a hollow bore 37 that runs through the centre of the piston 22. A first channel 38 extends radially from the hollow bore 37 through the piston head 24. The valve housing 21 includes a first passage 40 extending circumferentially around the inside wall of the valve housing 21. The piston 22, valve housing 21 and first passage 40 are configured such that when the piston 22 is in the first position (see FIG. 2), the inlet port 31 is fluidly communicated, via the hollow bore 37, the first channel 38 and first passage 40, with the first chamber 46 and thereby the third outlet 34. The piston 22, valve housing 21 and first passage 40 are also configured such that when the piston 22 is in the second or intermediate positions (see FIGS. 4 and 3), the inlet port 31, hollow bore 37, and the first channel 38 are blocked from the first passage 40 and thereby from the first chamber 46 and the third outlet 34.

A second channel 39 extends radially from the hollow bore 37 through the piston head 24. The valve housing 21 includes a second passage 41 which extends between the valve chamber 28 and the first outlet 32 and second chamber 47. The piston 22, valve housing 21 and second passage 41 are configured such that when the piston 22 is in the first or intermediate positions (see FIGS. 2 and 3 respectively), the inlet port 31 is fluidly communicated, via the hollow bore 37, the second channel 39 and the second passage 41, with the second chamber 47 and thereby the first outlet 32. The second passage 41 is of a sufficiently small cross-sectional area that it only allows a restricted flow of air therethrough when a supply of pressurised all is connected to the inlet port 31 and the valve 20 is in the first or intermediate positions. The piston 22, valve housing 21 and second passage 41 are also configured such that when the piston 22 is in the second position (see FIG. 4), the inlet port 31, hollow bore 37, and the second channel 39 are blocked from the second passage 41 and thereby from the second chamber 47 and the first outlet 32.

The valve housing includes a third passage 42 which extends between the valve chamber 28 and the second outlet 33 and third chamber 48. The piston 22, the valve housing 21 and the third passage 42 are configured such that when the piston 22 is in the second position (see FIG. 4), the inlet port 31 is fluidly communicated, via the hollow bore 37, the second channel 39 and the third passage 42, with the third chamber 48 and thereby the second outlet 33. The third passage 41 is sufficiently dimensioned that it allows a substantially unrestricted flow of air therethrough when a supply of pressurised air is connected to the inlet port 31 and the valve 20 is in the second position, or at least, a greater flow rate of air therethrough relative to the flow rate of air allowed through the second passage 41. The piston 22, valve housing 21 and third passage 42 are also configured such that when the piston 22 is in the first or intermediate positions (see FIGS. 2 and 3), the inlet port 31, hollow bore 37, and the second channel 39 are blocked from the third passage 42 and thereby from the third chamber 48 and the second outlet 33.

Although the valve housing 21 and piston 22 are manufactured so that they fit very closely together, there may still be small gaps between the piston 22 and valve housing 21, and between the valve housing 21 and the valve outer casing 30, through which air may leak. To prevent this leakage, rubber seals 60-70 are provided.

A first seal 60 is positioned, at the interface between the fourth outlet 35 and the first chamber 46, around the circumference of the fourth outlet 35 and in contact with the plug shaft 75 to prevent the unwanted escape of air from the first chamber 46 to atmosphere. Second and third seals 61, 62 are positioned around the outer perimeter of the valve housing 21 in contact with the valve outer casing 30, to prevent the flow of air between the atmosphere and the first and third chambers 46, 48 respectively. A fourth seal 63, positioned around the outer circumference of the first piston section 25, seals against the inside wall of the piston chamber 28 to prevent air from leaking between the first channel 38 and the second chambers 47. A fifth seal 64 is positioned around the outer perimeter of the valve housing 21 in contact with the valve outer casing 30 and between the first and second chambers 46, 47, to prevent the flow of air therebetween. A sixth seal 65 is positioned, around the outer perimeter of the valve housing 21 in contact with the inner surface of the valve outer casing 30 and between the second and third chambers 47, 48, to prevent the flow of air therebetween. A seventh seal 66 is positioned on the inside of the valve housing 21 around the inner perimeter of the recess 78 of the inlet port 31 and in contact with the piston shaft 23, to prevent the flow of air between the inlet port 31 and the section of the piston chamber 28 that surrounds the piston shaft 23. An eighth seal 67, positioned around the outer circumference of the third piston section 27 in contact with the inner wall of the valve housing 21, prevents the flow of air between the second outlet 33 and the section of the piston chamber 28 that surrounds the piston shaft 23.

The air control valve 20 includes a biasing means 76 comprising a coil spring positioned around the piston shaft 23 and which is configured to bias the piston 23 towards the first position.

The air control valve 20 includes a ninth seal 68 positioned around the outer circumference of the second piston section 26 and to the side of the second channel 39 closest to the inlet poet 31. When the piston 22 is in the first and intermediate positions, the ninth seal 68 is in contact with the inner wall of the valve housing 21 and seals the third passage 42 and the third chamber 48, and hence the second outlet 33, from the second channel 39. When the piston 22 is in the second position, the ninth seal 68 is disposed beyond the third passage 42 from the second channel 39 and so air can flow from the inlet port, via the hollow bore 37 and the second channel 39, through the third passage 42 to the third chamber 48 and hence to the second outlet 33.

The air control valve 20 includes a tenth seal 69 positioned around the outer circumference of the first piston section 25 to the side of the first channel 38 that is distal to the inlet port 31. In the intermediate and second positions of the piston 22, the tenth seal is in contact with the inner wall of the valve chamber 28 and blocks the first channel 38 from the first passage 40 and hence prevents the flow of compressed air from the inlet port 31 to the first chamber 46. However, when the piston 22 is in the first position, the tenth seal is aligned within the first passage 40 and so air can bypass the tenth seal, to allow the flow of air from the inlet port 31 to the first chamber 46.

The air control valve 20 includes an eleventh seal 70 disposed around the outer circumference of the second piston section 26 and to the side of the second channel 39 distal to the inlet port 31. Whilst the piston 22 is in the second position, the eleventh seal is in contact with the inner wall of the valve chamber 28 and blocks the second channel 39 from the second passage 41 and hence prevents the flow of air from the inlet port 31 to the second chamber 47 and to the first outlet 32. In the first and intermediate positions, the eleventh seal 70 is disposed beyond the second passage 41 from the second channel 39 and so air can flow from the inlet port 31, via the hollow bore 37 and second channel 39, to the second passage 41, to the second chamber 47 and hence to the first outlet 33.

The operation of the control valve 20 will now be described in use with an emergency breathing apparatus 10 as described previously. When a user wishes to use the breathing apparatus 10 of the invention, he opens the bag 17 and pulls out the respirator 12 and compressed air supply (not shown), and the automatic activation system opens the reducer valve (not shown) to allow compressed air to flow into the control valve 20. At this time, the piston 22 of the control valve 20 is held in the first position under the biasing force of the coil spring 76. The air enters the inlet port 31 via the supply hose 19 and flows through the hollow bore 37 of the piston 22 and into the first chamber 46, via the first channel 38 and the first passage 40. The compressed air in the first chamber 46 flows through the third outlet 34 and inflates the inflatable harness 14. The plug 75 blocks the fourth outlet 35, preventing compressed air in the inflatable harness 14 from escaping to atmosphere.

Whilst the piston 22 is in the first position, air also flows from the inlet port 31 into the second chamber 47 via the hollow bore 37, the second channel 39 and the second passage 41 of reduced diameter. The compressed air is supplied to the second chamber 47 at a restricted flowrate, due to the restrictive dimensions of the second passage 41. From the second chamber 47, the restricted flow of air flows out of the first outlet 32, through the sensing valve 80 and on to the interior of the respirator 12. This provides a continuous flushing flow of air to prevent toxic atmospheric gases from building up within the respirator mask 12 before it is donned by the wearer. The sensing valve 80 is configured to remain open until subjected to a predetermined threshold pressure, at which point it automatically closes. The sensing valve 80 is open upon initial activation of the breathing apparatus 10.

The compressed air in the first and second chambers 46, 47 acts on the first and second surfaces 43, 44 respectively, exerting a force on the piston 22 that opposes the force exerted by biasing means 76. Whilst the inflatable harness 14 is in the process of inflating, the force exerted on the piston 22 by the compressed air is weaker than the force exerted by the biasing means 76 on the piston head 24, and hence the piston 22 remains in the first position.

When the inflatable harness 14 becomes fully inflated the pressure in the first chamber 46 increases, as no further air can flow out of the third outlet 34, causing the force exerted on the first surface 43 to increase. The increased force exerted on the first surface 43 is sufficient to overcome the force of the biasing means 76, causing the piston 22 to shift towards the inlet port 31 (to the right hand side in FIGS. 2-4) and into the intermediate position wherein the flow of air to the head harness 14 is prevented, whilst a restricted flushing flow of compressed air continues to be supplied to the respirator mask 12 via the first outlet 32. Meanwhile, the head harness 14 is sealed from the inlet port 31 and remains in a fully inflated state as the plug 75 remains sealing the fourth outlet 35.

When the wearer dons the respirator mask 12, the seal 13 forms an airtight seal around the wearer's face and the flow of compressed air into the, now closed, volume of the respirator mask 12 causes the pressure within the respirator mask 12 to increase above atmospheric. The sensing valve 80 detects when the subsequent increased pressure within the mask 12 reaches the predetermined threshold pressure and then automatically closes, causing the pressure in the second chamber 47 to increase as the compressed air can no longer flow out of the first outlet 32. This causes the force exerted on the second surface 44 to increase. The increased force exerted on the second surface 44 causes the piston 22 to shift further towards the inlet port (to the right hand side in FIGS. 2-4) until it is in the second position.

Whilst the piston 22 is in the second position compressed air is supplied from the inlet port 31 to the third chamber 48, which is in fluid communication with the demand valve 50. The demand valve 50 supplies air to the respirator mask 12 whenever the user takes a breath. In the second position the flow of air from the inlet port 31 to the first and third outlets 32, 34 is prevented. Furthermore, once the piston 22 has moved into the third position as described above, the compressed air acts over the third piston surface 45 resulting in a pressure force on the piston 22 sufficient to overcome the biasing force of the coil spring 76 and thereby maintain the piston 22 in the second position The plug 75 includes a vent passage 77 formed as a recessed channel in an outer surface of a distal portion thereof. The vent passage 77 is configured so that when the valve moves into the second position, the vent passage 77 moves past the first seal 60 to fluidly communicate the fourth outlet 35 with the first chamber 46 and the third outlet 34, allowing the air in the head harness 14 to vent to atmosphere. This causing the head harness 14 to deflate and contract around the wearer's head, firmly securing the respirator 12 in place.

The respirator mask 12 remains in this operative position secured to a wearer's head allowing the wearer to safely breathe air from the supply via the control valve 20 and demand valve 50 and to evacuate the hazardous environment.

Although in the above described embodiment the control valve 20 comprises first, second and third outlets 32, 33, 34 such that the control valve may be used with a breathing apparatus comprising an inflatable head harness, it is also intended that an alternative embodiment of control valve (not shown) is to be encompassed within the scope of the invention. Such an alternative embodiment of control valve may omit the third outlet 34 described above. The control valve 20 may then be used, for example, with a breathing apparatus 10 that comprises a conventional head-strap harness as opposed to the inflatable harness 14 described above. Such an alternative embodiment of control valve would still comprise a first outlet fluidly communicated with the respirator 12, to provide a flushing flow of air thereto at a reduced flow rate, and a second outlet in fluid communication with a demand valve of the respirator to provide an unrestricted supply of compressed air at a relatively increased flow rate once the wearer has donned the respirator 12. In operation of such an alternative control valve, upon initial supply of compressed air to the inlet port 31, since there would be no third outlet and no inflatable head harness to inflate, the piston would immediately move to the intermediate position until the respirator mask is donned. All other features of such an alternative embodiment of control valve, and breathing apparatus including such a control valve, would be as described previously, and would function correspondingly.

Although embodiments of the invention have been shown and described above in the context of an 'escape set', it is intended that the invention is not limited to such application and may be used in any other type of breathing apparatus including 'working sets', self contained breathing apparatuses, and other such devices.

Although embodiments of the invention have been shown and described above by way of example only, the invention is not intended to be limited to these embodiments and is intended to include any combination of non-mutually exclusive features described above.

The invention claimed is:

1. An airflow control valve for use in a breathing apparatus to control a flow of air from a pressurized air supply to a respirator, wherein the airflow control valve comprises:
 a valve housing defining a piston chamber;
 a piston received within the piston chamber, comprising a hollow bore that runs through the piston;
 an inlet port for connection to a pressurized air supply, and
 first and second outlets, wherein the airflow control valve is configurable between:
 a first position in which the inlet port is in restricted fluid communication with the first outlet to allow a first flow of air from the inlet port, via the hollow bore of the piston, to the first outlet and in which the second outlet is sealed from the inlet port and,
 a second position in which the inlet port is in fluid communication with the second outlet to allow a second flow of air from the inlet port, via the hollow bore of the piston, to the second outlet, and wherein the first flow of air is more restricted than the second flow of air.

2. The airflow control valve according to claim 1, wherein the first outlet is sealed from the inlet port when the airflow control valve is configured in the second position.

3. The airflow control valve according to claim 1, wherein the airflow control valve includes a third outlet and is configured such that, in the first position, the inlet port is in fluid communication with the third outlet.

4. The airflow control valve according to claim 3, wherein the airflow control valve is configured such that, in the second position, the inlet port is sealed from the third outlet.

5. The airflow control valve according to claim 3, wherein the airflow control valve is configurable to a third position in which the inlet port is in restricted fluid communication with the first outlet and the inlet port is sealed from the second outlet and/or a third outlet; said airflow control valve further comprising:
 a fourth outlet, wherein the fourth outlet is in fluid communication with the third outlet when the airflow control valve is configured in the second position, and the fourth outlet is sealed from the third outlet when the airflow control valve is configured in the first position and the third position.

6. The airflow control valve according to claim 5,
 wherein the piston is slidable with the piston chamber between the respective positions and further comprises:
 a plug member configured to block the fourth outlet when the piston is in the first and third positions and to open the fourth outlet to allow flow of air therethrough when the piston is in the second position.

7. The airflow control valve according to claim 5,
 wherein the piston is slidable within the piston chamber between the respective positions; wherein the valve housing comprises a passage of restricted cross-sectional area which is in fluid communication with the first outlet and the piston chamber, and which is configured to allow the first flow of air from the inlet port to the first outlet when the valve is in the first position.

8. The airflow control valve according to claim 7, wherein said passage is a second passage and the valve housing further comprises first and third passages configured to fluidly communicate the inlet port with the third and second outlets respectively when the piston is in the first and second positions respectively.

9. The airflow control valve according to claim 1, wherein the airflow control valve is configurable to a third position in which the inlet port is in restricted fluid communication with the first outlet and the inlet port is sealed from the second outlet and/or a third outlet.

10. The airflow control valve according to claim 9, wherein the third position is intermediate the first and second positions.

11. The airflow control valve according to claim 1; wherein the airflow control valve is configured to a third position in which the inlet port is in restricted fluid communication with the first outlet and the inlet port is sealed from the second outlet and/or a third outlet; configured such that the airflow control valve is movable between the first, second and/or third positions in dependence of air pressure within the airflow control valve.

12. The airflow control valve according to claim 1, wherein the piston is slidable within the piston chamber between the respective positions.

13. The airflow control valve according to claim 12, wherein the inlet port, the first outlet, and the second outlet are formed in the valve housing in fluid communication with the piston chamber.

14. The airflow control valve according to claim 13 wherein the hollow bore is in fluid communication with the inlet port.

15. The airflow control valve according to claim 14, wherein the piston comprises:
a piston shaft and a piston head, wherein the hollow bore extends along a longitudinal axis of the piston shaft and a portion of the piston head.

16. The airflow control valve according to claim 14, wherein the piston includes a plurality of channels formed therein in fluid communication with the hollow bore and extending to an outer surface of the piston, and which are configured to selectively fluidly communicate the inlet port and the hollow bore with the outlets in the valve housing.

17. The airflow control valve according to claim 16, wherein the piston comprises a first channel configured to fluidly communicate the inlet port with a third outlet via the hollow bore when the piston is in the first position.

18. The airflow valve according to claim 17, wherein the piston comprises a second channel configured to fluidly communicate the inlet port with the first outlet via the hollow bore when the airflow control valve is in the first position, and to fluidly communicate the inlet port with the second outlet via the hollow bore when the piston is in the second position.

19. The airflow control valve according to claim 18, wherein the second channel is in the restricted fluid communication with the first outlet via the hollow bore when the piston is in an intermediate position.

20. The airflow control valve according to claim 12, further comprising:
a coil spring configured to bias the piston towards the first position.

21. The airflow control valve according to claim 20, wherein the piston comprises a plurality of piston surfaces configured such that pressurized air supplied to the inlet port can act upon one or more of the piston surfaces to exert a force against the coil spring.

22. The airflow control valve according to claim 21, wherein the valve is configured so that the piston slides from the first position to a third position when air pressure acting on a first piston surface reaches a first pre-determined value.

23. The airflow control valve according to claim 22, wherein the airflow control valve is configured so that the piston slides, from the third position, into the second position when air pressure acting on a second piston surface reaches a second pre-determined value.

24. The airflow control valve according to claim 1, further comprising:
a sensing valve fluidly connected to the first outlet and configured to close when an air pressure at the first outlet reaches a pre-determined threshold pressure.

25. A breathing apparatus comprising:
a respirator; and
an airflow control valve to control the flow of air from a pressurized air supply to the respirator, wherein the airflow control valve comprises:
a valve housing defining a piston chamber,
a piston received within the piston chamber, comprising a hollow bore that runs through the piston,
an inlet port for connection to the pressurized air supply, and
first and second outlets connected to the respirator, wherein the airflow control valve is configurable between:
a first position in which the inlet port is in fluid communication with the first outlet to allow a first flow of air from the inlet port, via the hollow bore of the piston, to the respirator via the first outlet and in which the second outlet is sealed from the inlet port and,
a second position in which the inlet port is in fluid communication with the second outlet to allow a second flow of air from the inlet port, via the hollow bore of the piston, to the respirator via the second outlet, and wherein the first flow of air is more restricted than the second flow of air.

26. The breathing apparatus according to claim 25, wherein the airflow control valve is configured such that when in the second position, the first outlet is sealed from the inlet port.

27. The breathing apparatus according to claim 25, further comprising:
an inflatable harness configured to secure the respirator to a wearer's head, the airflow control valve further being configured to control the flow of air from a supply to the inflatable harness.

28. The breathing apparatus according to claim 27, wherein the airflow control valve further comprises:
a third outlet connected to the inflatable harness, wherein the inlet port is in fluid communication with the harness when the airflow control valve is in the first position and wherein the inlet port is sealed from the inflatable harness when the control valve is in the second position.

29. The breathing apparatus according to claim 25, wherein the airflow control valve is configurable to a third position in which the inlet port is in restricted fluid communication with the respirator via the first outlet and the inlet port is sealed from the second outlet and/or a third outlet.

* * * * *